United States Patent [19]

Godin et al.

[11] 3,991,055
[45] Nov. 9, 1976

[54] LIQUID TRANSFER VALVE

[75] Inventors: Thomas J. Godin, West Hollywood; James Harrington, Fort Lauderdale, both of Fla.

[73] Assignee: Coulter Electronics, Inc., Hialeah, Fla.

[22] Filed: May 30, 1975

[21] Appl. No.: 582,302

[52] U.S. Cl. .................. 23/259; 23/230 B; 73/422 R
[51] Int. Cl.² .................. G01N 1/10; G01N 1/16; G01N 1/18
[58] Field of Search .............. 23/259, 253, 230 B, 23/254 R; 73/422

[56] References Cited
UNITED STATES PATENTS

| | | | |
|---|---|---|---|
| 2,846,121 | 8/1958 | Ronnebeck | 222/133 |
| 3,362,228 | 1/1968 | Stuben | 73/422 |
| 3,567,389 | 3/1971 | Coulter et al. | 23/259 |
| 3,567,390 | 3/1971 | Rothermel | 23/259 |
| 3,615,241 | 10/1971 | Low | 23/253 X |
| 3,819,330 | 6/1974 | Creighton | 23/254 X |

*Primary Examiner*—R.E. Serwin
*Attorney, Agent, or Firm*—Silverman & Cass, Ltd.

[57] ABSTRACT

A pneumatically operated liquid transfer valve assembly capable of segmenting and transferring plural different volumes of liquid from like numbered liquid flow paths established through the valve and depositing said segmented volumes into like numbered adjacent liquid flow paths under the influence of pressurized fluid. At least two pairs of liquid flow paths are established and a linearly movable valve element carrying at least two pairs of segmenting bores is arranged selectively to intercept said pairs of liquid flow paths. One of each segmenting bore pairs intercepting one of each pair of liquid flow paths at one condition of the valve and the valve element being translated linearly to place said one of each segmenting bore pair in communication with the other of each liquid flow path pair with the other of each segmenting bore pair intercepting said one of each liquid flow path pair; the members of each segmenting bore pair being identical in volume but each bore pair being different in volume. Sealing of valve elements is obtained by maintenance of close clearances and a lubricating system is provided capable of supplying lubricant from reservoirs to the bearing surfaces within the valve simultaneously with each operation of the valve. The segmented volumes of said segmenting bores are provided by selection of the length and diameter of the bores. A pin and groove coupling is utilized to maintain the movement of the valve element linear.

85 Claims, 7 Drawing Figures

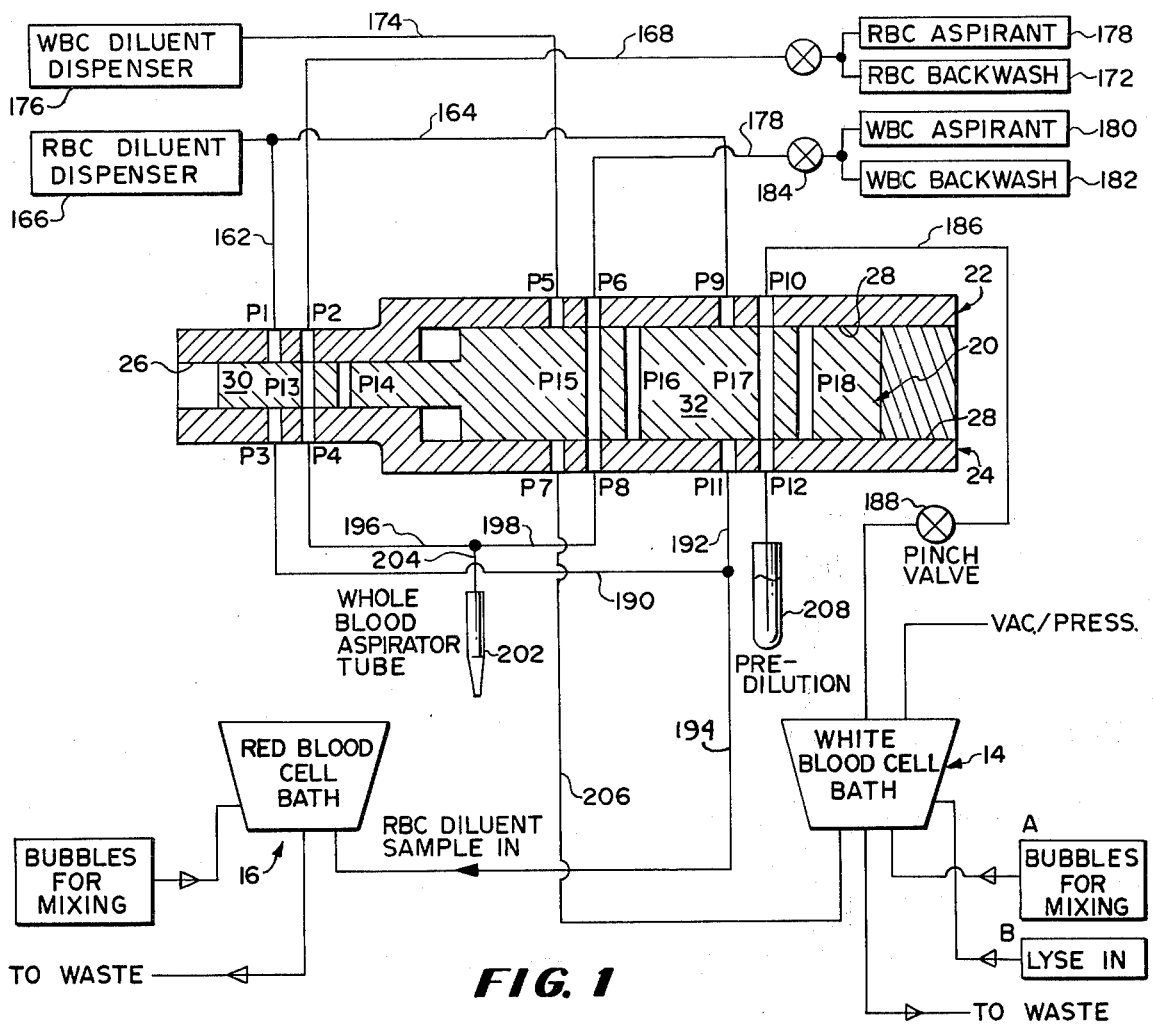
FIG. 1
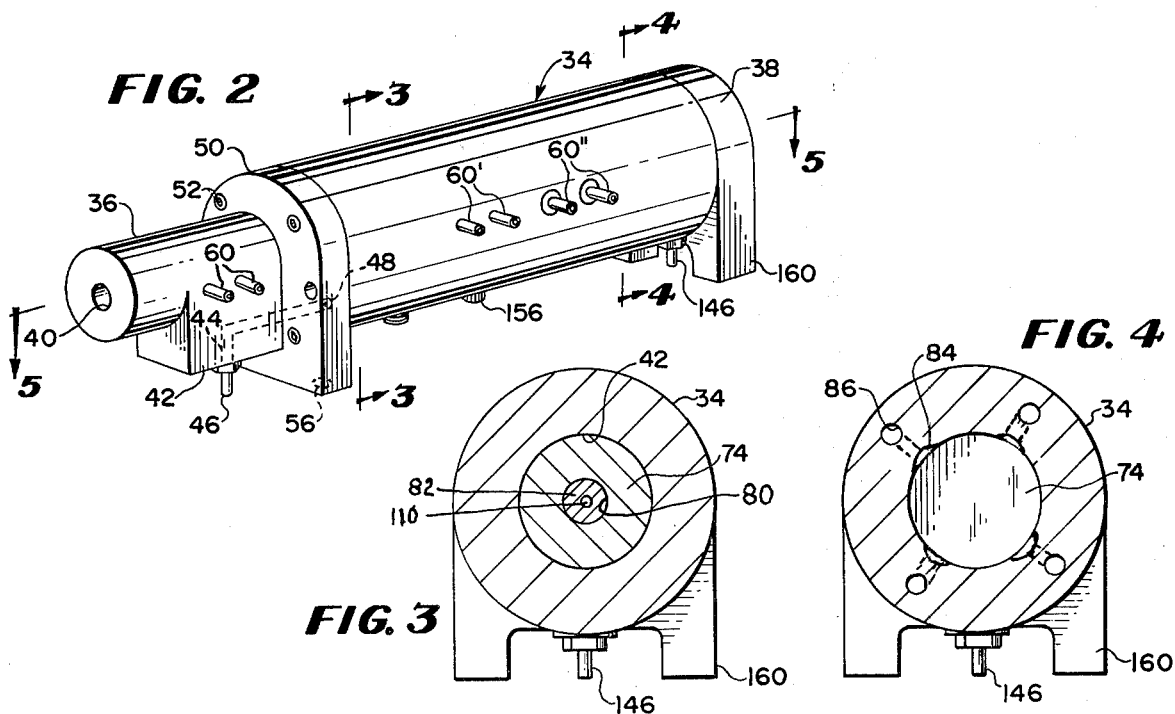
FIG. 2
FIG. 3
FIG. 4

LIQUID TRANSFER VALVE

BACKGROUND OF THE INVENTION

1. Field of the Invention

This invention relates generally to liquid transfer systems and more particularly provides a pneumatically operated liquid transfer valve having a linearly movable valve element carrying segmenting passageway pairs of different volume so thaat at least two desired segments of a single sample can be obtained simultaneously in the absence of a two step segmentation heretofore characteristic of earlier transfer valves.

2. Description of the Prior Art

In the U.S. Pat. No. 3,549,994, there was provided a structure in which a sample of blood is drawn into a fluid system in which it is accurately diluted with a suitable diluent and divided into two samples for red and white blood cell determination. The red sample for red cell determination is counted and sized utilizing a COULTER scanning device and is discharged, while at the same time the other is lysed to break up the red cells and subjected to another COULTER electronic scanning device for a white cell count with the simultaneous examination of the sample for hemoglobin determination and discharge. The trademark COULTER is a registered trademark, Registration No. 995,825, owned by Coulter Electronics, Inc. of Hialeah, Florida, U.S.A.

Processing is automatic and continuous for samples drawn into the apparatus at intervals exceeding at least a certain minimum time duration. The structure therein disclosed included means for combining the data automatically to ascertain certain of the parameters which are susceptible of derivation from determinations made, and producing data corresponding to all of the parameters both determined and derived from the apparatus. These parameters were blood counts, sizes, percentages, and the like, accepted in the medical arts as aids for diagnosis, treatment, and research. The structure therein disclosed utilized vessels, valves, and connecting conduits for the intermixing and/or diluting of fluids primarily for the purpose of making measurements and tests on such fluids. Of course, it should be appreciated that such description is somewhat general and while primarily utilized with an automatic instrument such as disclosed in the above-identified patent which employs the electronic particle analyzing apparatus operating upon principles disclosed in U.S. Pat. No. 2,656,508, it is capable of many uses. In medicine, biology, chemistry, and allied fields, research as well as routine testing required the use of apparatus which can produce fluid mixtures of specific concentrations accurately and automatically and particularly, can feed known quantities of fluids to a selected ones of a plurality of locations.

In the apparatus referred to in U.S. Pat. No. 3,549,994, samples of whole blood were introduced one every 15 seconds. The apparatus performs the requisite dilutions, tests, and computations needed for obtaining blood counts of white and red cells, a hematocrit determination, a hemoglobin measurement, and so on. Accordingly, such automatic instrument is required quickly and accurately to prepare the necessary sample suspensions of predetermined concentration for transfer to the testing apparatus of the instrument. Liquids must be pumped, transferred and moved between vessel and it is with such type of liquid transfer apparatus that this invention is concerned.

One type of the liquid transfer valve structure has been disclosed in U.S. Pat. No. 3,567,390 and that particularly consisted of a central element and a pair of outer elements engaged against opposite faces of the central element to sandwich same therebetween. The central element is movable relative to the other element between first and second positions. At least one measuring conduit is formed in the central element and at least a pair of ports are provided in each outer element. Each of the ports in one of the outer elements aligns with a port carried by other outer element so that two fluid paths are defined. The central member is indexed to a first position to align one measuring conduit with one of said fluid paths for reception in that one conduit of a portion of the fluid sample. The central element then is moved to a second position. By virtue of such movement, the volume of the sample in the measuring conduit is segmented and deposited in the other fluid path for combining with a diluent introduced therein so as to provide a precise dilution.

In the various fluid transfer valve constructions disclosed in the aforesaid patents, the movable element is either pivoted or rotated or both to effect the segmenting of the precise volume quantities of sample. Further, in some of said earlier valve constructions a second or companion segmenting passageway is provided. Immediately subsequent to the delivery of the first sample for the first testing apparatus forming the first dilution, the first step of the second dilution is effected by drawing to the companion segmenting passageway, a precise volume of said first dilution, thereafter actuating the valve to deliver a precise volume of first dilution to a second testing apparatus along with a predetermined volume of diluent thereby to effect a second dilution. The first dilution is utilized for the purpose of making white blood cell evaluations as well as hematocrit through the process of lysing the red blood cells from the sample. The second dilution is utilized to evaluate the red blood cells, for example, which requires a substantially more dilute sample. It would be advantageous and of course more efficient, simultaneously to direct the proper dilutions to testing apparatus so that both operations, that is the white blood cell determinations and the red blood cell determinations can be carried out substantially simultaneously on the same sample. The previously available liquid transfer valve means for effecting the double dilutions contemplate a seriatum operation where for each sample the white blood cell evaluation is determined and thereafter the red blood cell evaluation is determined.

In addition, the fluid transfer valve constructions heretofore referred to include associated therewith plural drive components and elements that require maintenance of very close tolerances in the course of manufacture. Failure to meet those close tolerances would result in either inaccurate alignment, movement and the like effecting the accurate measuring and transfer of the liquid. Relatively complex means was required to cleanse and to drain the valve passageways so that successive samples were not contaminated. Difficulties in loading as well as dispensing provide the impetus for improvement. Simplification of the heretofore known valve structures so as to perhaps reduce the cost yet maintain the necessary accuracy is a continuing problem.

Accordingly, a fluid transfer valve is sought which can effect at least two different degrees of dilution from a single sample simultaneously and with conservation of sample and diluent.

It has been increasingly common to obtain relatively small whole blood samples using micropipettes sometimes referred to a finger-sticks. Separate valving and feeds were required to perform the desired analysis of such samples since the volume of sample involved is small. Ordinarily, the finger-stick was introduced to a precise volume of diluent in a separate vessel. A small fraction was taken for further dilution while the remainder was treated for other analyses and introduced to other testing apparatus.

A need thus arises for a fluid transfer valve which can allow the operator to choose between segmenting operation on a whole blood sample or a prediluted sample without using separate valving, considerable increase in fluid lines, etc.

Attention should be directed also to the need to provice a separate vessel in at least one testing apparatus, that is, for white blood cell determinations so that the first dilution could be made without lysing since a portion thereof would have to be used to make the second dilution. The advantages of providing a valve where the original blood sample could be utilized to provide both dilutions are evident, with particular advantage gain in permitting lysing and the mixing to take place in a single vessel which can be the bath in which the testing is performed.

SUMMARY OF THE INVENTION

A liquid transfer packless spool valve for use in a diluting system and comprising a movable valve element slidably sealingly sandwiched between a pair of opposed facing conforming surfaces for frictionally slidable movement therebetween, said valve element having at least two spaced pair of parallel through bores and said stationary surfaces having ports opening thereto and to the exterior of the valve defining fluid flow paths, the valve element being movable between a first position where said bores are each aligned with one of each set of ports and a second position where each of said bores are aligned with each of the ports of said pairs associated therewith, the bores of each pair being of like volume and each pair of bores having different volumes. Clearances between said element and surfaces are of the order of 10 to 90 millionths of an inch making packing unnecessary. Means are provided to drive the movable element along a solely linear path and between first and second positions, and means to limit the length of the path to the distance between axial centers of the bores of each pair, the movable element being driven by application of pressurized fluid applied alternately to one end of said movable element while simultaneously venting the opposite end. An additional set of segmenting bores and an associated port pair are provided to enable selected use of the same valve with a prediluted sample. A lubrication system including an in-valve reservoir and pump means is provided for lubricating the element simultaneously with operation of the valve. The invention contemplates provision of one pair of flow paths and one segmenting passageway with the spool valve used as a simple segmenting valve.

BRIEF DESCRIPTION OF THE DRAWINGS

FIG. 1 is a diagrammatic representation illustrating the general operation of the liquid transfer valve constructed in accordance with the invention as employed in a fluid handling system of an automated analytical apparatus;

FIG. 2 is a perspective view of a liquid transfer valve constructed in accordance with the invention;

FIG. 3 is a sectional view taken along lines 3—3 of FIG. 2 and in the direction indicated;

FIG. 4 is a sectional view taken along lines 4—4 of FIG. 2 and in the direction indicated;

DESCRIPTION OF THE PREFERRED EMBODIMENTS

Figure 5:
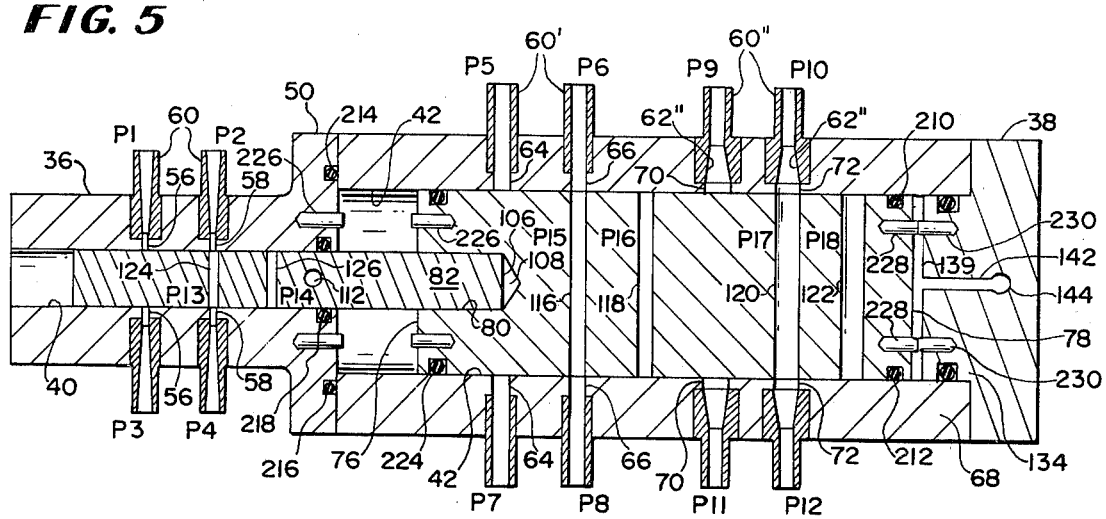
FIG. 5 is a diagrammatic sectional view of the transfer valve of FIG. 2 illustrating in one position assumed during operation.
Figure 6:
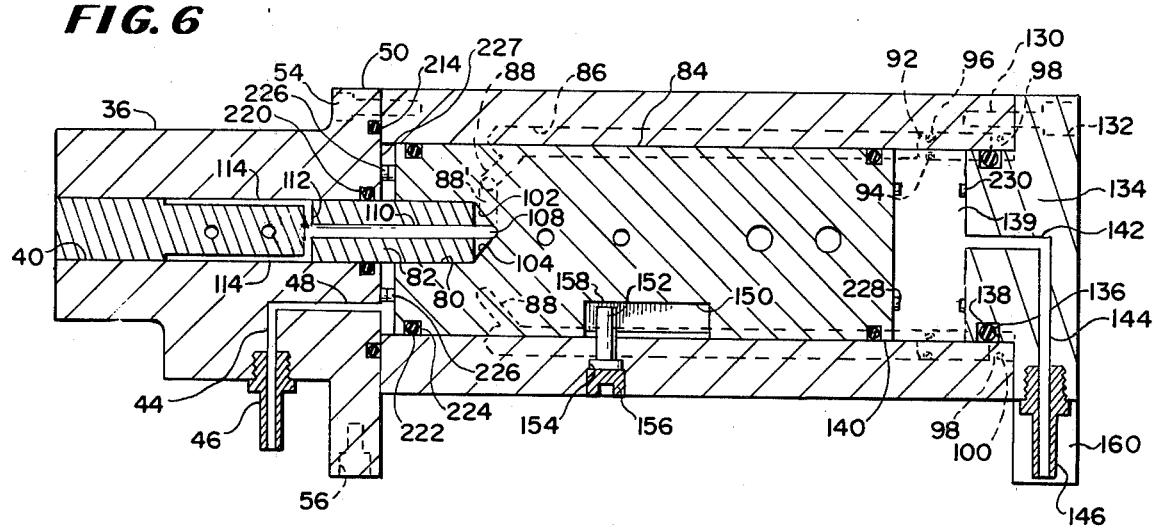
FIG. 6 is a view similar to that of FIG. 4 rotated 90° and illustrating the condition of the valve in the second or other position assumed during the operation thereof.
Figure 7:
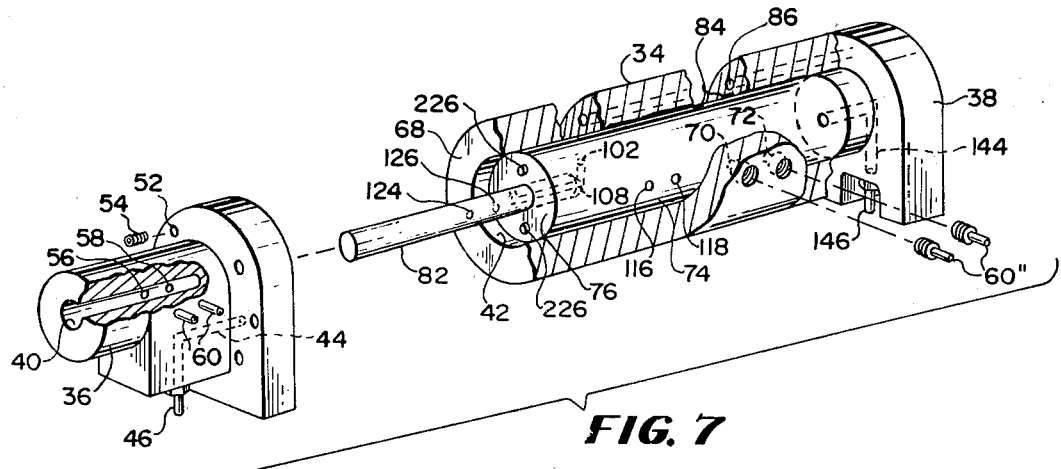
FIG. 7 is an exploded view of the liquid transfer valve according to the invention, portions deleted and portions shown in section to illustrate interior detail.

Generally, the fluid transfer valve as will be described herein is capable of delivering from a single sample, at least two different volume segments simultaneously for dilution with diluent by providing means for establishing at least two pairs of fluid paths traversed by two pairs of precise measuring bores which selectively segment a known volume from each of said pairs of paths and deliver that segment to the other of said pairs of paths. The pairs of measuring bores differ one pair from the other in that they carry different volumes and hence segment different volumes of fluid. Means are provided to introduce the same given volume of diluent to each of the other fluid paths whereby the dilutions delivered from each of said pair of measuring bores is determined entirely by the volume of the said bores. Means are provided to rinse one of the members of each pair of measuring bores simultaneously with the delivery of the pair of dilutions from the other of each pair. Means are provided to drive the valve by pressurized air and to lubricate the bearing surfaces of the valve while it is being driven.

The fluid transfer valve constructed in accordance with the herein invention can function as a valve as used in a diluting system such as employed in the apparatus disclosed in U.S. Pat. No. 3,549,994 granted Dec. 22, 1970 to Rothermel et al., and is an improvement upon the fluid transfer valve structures disclosed in U.S. Pat. Nos. 3,567,389 and 3,567,390 issued to Coulter et al. and to Rothermel respectively on Mar. 2, 1971, all three patents being owned by the assignee of the herein application. Reference can be made to these patents for description of the general apparatus within which the fluid transfer valve of the invention is intended to function and as well as to afford general information as to the functions which the system as a whole seeks to accomplish. The apparatus referred to in the above-identified patents operate in a mode that differs from that within which the fluid transfer valve of the invention is intended to function. While generally the results are similar, the mode of the invention involves simultaneous rather than successive operation upon first one dilution and then second dilution of said sample. Accordingly, the fluid transfer valve of the invention delivers two different volumes of the same sample simultaneously to two different locations so that the respective tests can be performed simultaneously. Further, the fluid transfer valve according to the invention is capable of receiving not only an original, raw sample, but, without change, is capable alternatively of receiving and passing a pre-diluted sample directly to one testing apparatus while still capable of segmenting and transferring a predetermined quantity thereof to another testing apparatus.

One significant characteristic of the fluid transfer valve of the instant invention is the provision of precise measuring bore pairs formed in a movable element which includes portions of different diameter, said measuring bore pairs being formed respectively in the portion of lesser diameter and in the larger diameter portion so as to vary the volume measured by each of the measuring bores. Bore pairs are provided so as to facilitate rinsing of one sample prior to drawing of a second sample. The movable member is actuated by application of fluid pressure alternately against the ends of the wider diameter portion by providing means for introducing pressurized air from a source to said end surfaces; a lubrication system being provided which is operable to lubricate the bearing surfaces during operation of the valve.

In the interest of understanding the type of determinations performed in apparatus utilizing the fluid transfer valve of the invention, the specification of each of the aforesaid mentioned patents respectively is incorporated herein to the extent required by one skilled in the art to understand the system and functions performed thereby as well as by the improved fluid transfer valve herein disclosed.

Generally, a fluid sample for dilution, such as human blood, is obtained in any convenient manner. The sample is introduced into a vessel. A tube or snorkel is dipped into the vessel and draws sample therefrom into the fluid transfer valve of the system, said valve being designated generally by reference character 10. The sample is introduced into the valve 10 at two locations and two different volume slugs of said sample are segmented by operation of said valve 10 and thereafter are delivered to two different locations by flushing out the slugs with the same quantity of diluent, delivering the resulting volumes to two different locations. The greater degree dilution of the small slug is formed in a testing apparatus for performance of a first series of tests, and, simultaneously the larger volume slug which is diluted to a lesser degree is delivered simultaneously to a second testing apparatus. Therefore, generally, where two diluting operations heretofore have been employed in the patented fluid transfer valve constructions, the operation of the fluid transfer valve 10 effects a single diluting operation yet with production of two different degrees of dilution simultaneously.

It should be understood that although the fluid transfer valve of the invention is described as employed in certain identified analytical systems, this is merely by way of illustration and does not so limit the present invention to blood sampling.

Referring again to FIG. 1, the general system for fluid handling is connected with testing apparatus operating in accordance with the principle taught in U.S. Pat. No. 2,656,508 for determination of various parameters of blood cell characteristics. A first apparatus is indicated generally by block 14 and a second testing apparatus is represented generally by block 16. Actual dilutions, that is mixing and adding of reagents when necessary, is performed in one vessel of each testing apparatus. The fluid transfer valve according to the instant invention is coupled to the aforesaid apparatus by fluid lines which will hereinafter be described. For ease in description, the diagrammatic representation of the fluid transfer valve 10 as shown in FIG. 1 can be described in terms of a sandwich wherein a central linearly movable valve element 20 is sandwiched between a pair of like facing stationary elements 22 and 24. The movable element 20 has a portion of reduced thickness relative to the remaining portion thereof. The stationary elements are arranged apart only sufficiently to accommodate the movable element 20 therebetween with very close clearance, the clearance between the slidable element 20 and the respective stationary elements 22 and 24 is minimized, to a degree on the order of magnitude of 10 to 90 millionths of an inch. A suitable lubricant such as silicone lubricant (grease or oil) is utilized between the facing surfaces so as to prevent binding of the bearing surfaces concerned (during movement).

For the purposes of description, the sandwiching elements 22 and 24 can be said to define therebetween a first chamber 26 and a second chamber 28. The sandwiched element has a first portion 30 and a second thicker portion 32. The portion 32 has a linear dimension less than the length of chamber 28. The outer members 22 and 24 each have pairs of passageways formed therein leading from the exterior surfaces to the chambers 26 and 28. A first pair of passageways P1 and P2 are formed in the member element 22 and communicate to the chamber 26 and a pair of like matched passageways P3 and P4 are formed in member 24 in alignment with passageways P1 and P2. A pair of like parallel passageways P5 and P6 are formed in stationary element 22 opening to chamber 28 and, likewise, a pair of matching passageways P7 and P8 are formed in stationary element 24 aligned respectively with passageways P5 and P6. A third pair of passageways P9 and P10 are formed in stationary element 22 at a location spaced from the passageways P5 and P6 and, likewise, matching passageways P11 and P12 are formed in stationary element 24 in alignment with passageways P9 and P10.

The slidable element 20 carries three pairs of measuring bores, each pair being of different volume but comprising parallel precise matched bores respectively. One pair of said measuring bores is formed in portion 30 of slidable element 20 and of course is of lesser length than the measuring bore pairs formed through the thicker portion 32 of element 20. Thus, measuring bores P13 and P14 are formed in portion 30 while measuring bores P15 and P16 as well as pairs P17 and P18 are formed in portion 32 of slidable element 20. The spacing between the central axes of passageways P1 and P2, P3 and P4 is the same as the spacing between central axes of measuring bores P13 and P14. The axial spacing between passageways P5 and P6 and measuring bores P15 and P16 are identical and likewise, the axial spacing between passageways P9 and P10 is the same as the axial spacing between passageways P17 and P18. The lineal path traversed by the slidable element 20 has a value equal to the axial spacing between the measuring bores making up each pair. Therefore, in one position of the slidable element 20, passageways P13 and P14 are aligned respectively with the passageways P1 and P3 and P2 and P4. In the same position of the valve, the passageways P5, P15 and P7 are aligned and passageways P6, P16 and P8 are aligned. Likewise, in the same position of the slidable element 20, passageways P9, P17 and P11 are aligned as are passageways P10, P18 and P12.

One specific embodiment of the invention is illustrated in FIG. 2 and is designated generally by reference character 10. The valve assembly 10 comprises a movable element 20 (FIG. 1), a hollow sleeve 34, an end cap 36 and a cover 38. Sleeve 34 carries through axial passage 42 open at opposite ends thereof. End cap 36 carries a through axial passage 40. Passage 42 is of larger diameter than passage 40 with the sleeve and end cap being secured so that the passages 40 and 42 are coaxial. An angular passage 44 is provided in the end cap 36 and a fitting 46 is secured at its entrance. The opposite end 48 of passage 44 opens to the passage 40. A flange 50 is provided on the end cap 36, suitable passageways 52 being formed therein to facilitate securement of the end cap 36 to the sleeve 34 by cap screws 54. Suitable threaded sockets 56 are formed in the flange 50 for mounting the valve assembly 10 to a panel of the instrument with which it is to be associated. Both passageways 40 and 42 respectively are of precise inner diameter.

Two pairs 56, 58 of passageways are formed through end cap 36 respectively communicating to passage 40 at diametrically opposed locations. Passageways 58 are parallel to passageways 56 and are linearly aligned therewith. The axes of passageways 56 and 58 follow a line taken through the axis of passage 40. Suitable fittings 60 are provided for reception into the passageways 56 and 58 from the exterior of end cap 36 so as to facilitate coupling of said passageways to suitable conduits. The fittings carry through conduits 62 inwardly tapered to facilitate communication with the segmenting bores to be described.

A pair of opposite aligned passageways 64 and a second pair of opposite aligned passageways 66 are formed through the wall 68 of sleeve 34 along lines intersecting the center axis of passage 42. Passageway pairs 64 and 66 are spaced apart the same lineal distance, center to center, as the spacing of passageways 56 and 58. Additional passageway pairs 70 and 72 are formed through the wall 68 of sleeve 34 and communicate to the interior of passage 40, the bore pairs 70 and 72 having their axes spaced linearly the same distance as the axial spacing between bore pairs 56 and 58 and bore pairs 64 and 66. Suitable fittings 60' and 60" are inserted into the passageway pairs 64, 66 and 70, 72 respectively to establish a coupling for conduits from the exterior of the valve 10. Thus, the stationary elements 22 and 24 of the valve diagrammatically illustrated in FIG. 1 finds equivalence in the assembly resulting from the coupling of sleeve 34 with end cap 36 with passage 40 and 42 coaxial and the passageway pairs respectively carried thereby linearly aligned in parallel disposition. Fittings 60' and 60" have appropriately cross-section conduits 62' and 62" to aid in communication.

The movable element 20 of the valve 10 illustrated in FIG. 1 diagrammatically finds its physical embodiment in a spool or plunger 74 having a lineal dimension less than the length of the passage 40 at least by an amount equal to the spacing between axes of the respectively matched passageway pairs. The spool 74 has opposite end faces 76 and 78. The spool 74 also has an axial passage 80 opening to end face 76 and a cylindrical rod 82 is seated tightly therein. The spool 74 as well as the rod 82 are precisely formed and respectively have outer diameters only slightly less than the inner diameters of the respective bores 42 and 40. The diameter of passageway 42 and the outer diameter of spool 74 differ in the order of magnitude by an amount about 30 to 90 millionths of an inch. Likewise, the outer diameter of rod 82 is less than the diameter of passageway 40 by an order of magnitude also 30 to 90 millionths of an inch. A lubricant is provided for the bearing surfaces of the spool 74 and the sleeve 34 to permit relative slidable movement thereof without binding. The inner surface of wall 68 of sleeve 34 has linearly extending shallow channels 84 circumferentially spaced about the axis of the passage 42, the ends of the channels 84 being spaced from the opposite ends of the sleeve 34. Preferably channels 84 are of crescentlike cross section. Blind bores 86 are formed in the wall 68 of sleeve 34 opening to end of said sleeve. The bores 86 are arranged about the sleeve substantially co-extensive with the channels 84 but their blind ends are just short of the inner ends of said channels 84. Angled passages 88 respectively link bores 86 with their adjacent channels 84. Cylindrical pins 90 are disposed in the open ends of bores 86 spaced inward a small distance from the open end. Each pin 90 includes an enlarged portion 92 carrying an annular groove 94 in which an O-ring 96 is seated. The outer diameter of the O-ring 96 is slightly greater than or at least the same as the diameter of bore 86 so that a fluid-tight seal is established. A stub pin 98 also carrying an O-ring 100 caps the bores 86. Portion 92 can be termed a piston.

The bores 86 are filled with a viscous silicone oil or silicone grease or other suitable chemically resistent lubricant.

One, 88' of the angled passageways 88 also communicates to a passage 102 which is formed in the spool 76 and communicates to the base or inner end 104 of axial passage 80, said end 104 being conical in configuration and with the insert end 106 of rod 82, defines a minichamber 108. An axial bore 110 is formed in rod 82 leading from end 106 to a diametric passage 112 opening to a pair of shallow grooves 114 formed along the length of rod 82. Silicone grease or other suitable lubricant also is introduced along the path defined from the angled passage 88' to the chamber 108 thence along axial bore to the grooves 114.

The spool 74 and rod 82 are slidable, respectively, in a linear direction within passages 42 and 40. Means are provided for limiting the stroke of the spool and means also are provided to restrict its movement only to the linear direction.

The spool 74 contains precise measuring or segmenting through bores 116 and 118 as well as segmenting bores 120 and 122. The cylindrical rod 82 has fine through segmenting bores 124, 126. The bores 116 through 126 are axially parallel and pass through the center axes respectively of the plunger 74 and rod 82. The spacing between bores 116, 118, 120 and 122, and 124 and 126 is equal to the axial spacing between the associated passageway pairs formed in the sleeve 34 and end cap 36 respectively. Segmenting bores 116 and 118 are of identical diameter and length. Segmenting bores 120 and 122 are of greater but identical inner diameter and the same length as bores 116, 118. Segmenting bores 124 and 126 are identical in inner diameter, much lesser than the others and, of course, have lengths less than the others. Thus, the volumes subtended by segmenting bores 116 and 118; 120 and 124; and 126 and 128 are precise and respectively different. The segmenting bores 116 and 118, and 120 and 122 each contain a volume to effect a lesser dilution with a given quantity of diluent while the volume of segmenting bores 124 and 126 is selected to provide a greater dilution with the same volume of diluent. The channels 84 are located so as not to interfere with the passageways or bores. The respective segmenting bores formed in the spool are axially aligned with the matching passageways formed in the sleeve 34 and cap 36 respectively. The end of sleeve 34 opposite end cap 36 is closed off by a cover 38 fastened thereto by suitable fastening means 130 secured in passageways 132. The cover 38 has a cylindrical portion 134 which enters the passage 40 and has a groove 136 carrying an O-ring 138 for sealing off the interior of said passage 40. The height of portion 134 is selected to leave a chamber 139 which communicates to passages 140 leading to the pistonlike portions 92. An axial passage 142 is formed in the cylindrical portion 134 of cover 38 opening to the chamber 139. A radial passage 144 communicating to passage 142 is formed in the cover 38 and is capped at the exterior opening 144 thereof by fitting 146. Fittings 46 and 146 are adapted to be coupled to a source of compressed air, preferably under 50 psi pressure.

In the operation of the valve, said compressed air is introduced from a source to fitting 146.

The pistons 92 forceably are translated to compress the grease in bores 86 and force same into the channels 84 from whence distribution is made to portions of the bearing surfaces. The compressed air also impinges upon end face 78 of spool 74, urging said spool to the left, as illustrated, at the same time that the grease in bores 86 is pressurized.

The spool 74 is provided with a groove 150. Guide pin 152 is set into a suitable socket 154 formed in the sleeve 34 and held by setscrew 156, so that the end 158 rides within the groove 150, the walls of which just accommodate said end 158. In this manner, the reciprocable movement of spool 74 maintained linear in a single path. In operation fittings 46 and 146 are coupled to a source of pressurized fluid such as compressed air, so that the plunger 76 is movable under the force of said compressed air (preferably 50 p.s.i.) impinging against the face 76 of the plunger in one operation and face 78 of the spool 74 in the return operation. Cover 38 has foot portions 160 which carry suitable sockets cooperating with the sockets 56 in flange 50 for securement of the valve unit onto the panel of the instrument with which it is to be utilized.

As installed in the system represented diagrammatically in FIG. 1, there are fluid lines leading between the valve assembly and elements of the diluting as well as the testing system. Lines 162 and 164 couple passageways P1 and P9 to a source 166 for dispensing a predetermined volume of diluent to passageways P1 and P9. Fluid line 168 connects the passageway P2 with a source of vacuum 170 and a source of diluent 172 alternatively through suitable valve means. Line 174 connects passageway P5 with diluent dispenser means 176 for dispensing to passageway P5 of a given volume of diluent. Line 178 connects passageway P6 to a source of vacuum and a source of diluent alternatively, respectively designated by reference characters 180 and 182 through suitable valve means 184. Line 186 connects passageway P10 with the testing apparatus 14 through a suitable valve 188.

Lines 190 and 192 connect passageways P3 and P11 respectively to line 194 which leads to testing apparatus 14. Lines 196 and 198 respectively connect passageways P4 and P8 with a whole blood aspirator 202 from a container (not shown) through line 204. Fluid line 206 couples passageway P7 to testing apparatus 14. In the system that is diagrammatically represented in FIG. 1, testing apparatus 14 provides white blood cell determinations while testing apparatus 16 provides red blood cell determinations.

The valve 10 operates between two positions, a first position for loading the measuring passageways thereof and a second position for dispensing the loaded quantities. Since the loading is effected by coupling from a source of sample through the valve to a source of vacuum, the first position can be described as an aspirating position. The dispensing is performed by feeding a given quantity of diluent to the valve passageways driving the subtended quantity or volumes of sample to their respective destinations. The second position therefore can be described as a delivery or dispensing position. At the same time that the segments are swept out, diluent is introduced to rinse the originally utilized passageways of the sleeve 34 and end cap 36. This procedure is called a backwashing since the respective lines concerned are coupled to their source so that when diluent is passed therethrough the source lines are washed out. By utilizing the valve 10 in the mode of operation described, intermingling, other contamination, etc., of one sample with another, is practically eliminated.

In the first or aspirating position of valve 10, the passageways P2, P13 and P4 are aligned as are passageways P6, P15 and P8 and passageways P10, P17 and P12. Passageways P1 and P3, passageways P5 and P7 and passageways P9 and P11 are blocked off respectively by the solid portions of rod 82 and spool 74.

When the valve 10 is in the aspirate position, whole blood is drawn by aspirator 202 along line 204, and then to lines 196 and 198, thence simultaneously through the fluid path defined by passageways P4, P13 and P2 and the fluid path defined by passageways P8, P15 and P6. Then, the valve 10 is actuated by a pulsed application of 50 p.s.i. compressed air for a duration of about 1.5 secs. to its delivery or dispensing position where passageways P1, P13 and P3 are aligned and passageways P2, P14 and P4 are aligned. Likewise, passageways P5, P15 and P7 are aligned and passageways P6, P16 and P8 are aligned. A predetermined volume of diluent then is introduced along lines 164 and 162 to passageways P1 and P9 and along line 174 to passageway P5. The slug of sample in P13 which has been subtended on the operation of the valve 10 to its dispense position is driven to and along line 190 and 194 to testing apparatus T2. The slug in passageway P15 is driven along line 206 to testing apparatus T1 simultaneously with the delivery of the subtended slug of P13 to testing apparatus T2. At the same time that the deliveries are effected, diluent is back-washed along line 168 and 178 to wash out passageways P2 and P4, and as well, through passageways P6 and P8 back to lines 196 and 198 via line 204 to and through the aspirator 202.

Where the predilution sample is used, the only passageways of the valve used are P9, P17, P11, P10, P18 and P12 and no sample is aspirated from the whole blood sample container. Valve 188 is opened to permit predilution sample to be drawn from container 208 to passageway P17 in the first position thus delivering same to testing apparatus 14. When the spool 74 is pulsed to its second position, the subtended slug from passageway P17 is delivered into the fluid path defined by aligned passageways P9, P17 and P11 and by way of lines 192 and 194, to the testing apparatus 16. The remaining liquid content of the vessel 208 is flowed along the fluid path defined by aligned passageways P12, P18 and P10 to testing apparatus 14 by way of line 186.

The valve 10 has its respective segmenting passageways formed as to subtend the following volumes:

Passageways P13 and P14 each contain a volume of 1.6 microliters;
Passageways P15 and P16 each contain a volume of 44.0 microliters; and
Passageways P17 and P18 each contain a volume of 351. microliters.

The volume of diluent dispensed to the three pairs of passageways is equal to 10 cc (isotonic water being used) so that a dilution of 6250 to 1 is provided for testing apparatus T2, this being required for the red blood cell determinations in testing apparatus 16 while the dilution to be effected in testing 14, where there are white blood cell determinations, is such that with the addition, in the testing apparatus, of lysing agent, the dilution is 250 to 1. The volume subtended by passageway P17 and combined with 10 cc of diluent provides a 6250 to 1 dilution for operation within the testing apparatus 16. All mixing is performed in a single vessel of each testing apparatus, with suitable lines for air mixing and reagent addition, respectively A and B where necessary being provided to said vessels. Preferably, the mixing, etc., is performed in the aperture baths.

The volume lost in passageway P17 is accounted for in determining the necessary dimensions of the passageway. Likewise, the volume of subtended diluent is considered in calculating the volume of whole blood sample to be subtended.

In the embodiment described, the diameters of passageways P13 and P14; P15 and P16; and P17 and P18 are respectively 0.0225 inches, 0.0636 inches and 0.1810 inches.

The diameter of rod 82 is 0.2455 inches and the diameter of spool 74 is 0.8446 inches.

The diametrical clearance of approximately 0.000050 inches between the spool 74 and the passage 40 of sleeve 34 is found to be sufficient clearance for the traversal of the linear path while restricting communication of the liquid between the respective segmenting bores and passageways, The valve parts are formed of the same aluminum alloy and is provided with an antifriction coating such as polyfluorethylene.

The rod 82 is seated permanently in the socket defined by axial passage 80. Also, the various parts must be properly sealed both against liquid and especially against leakage of pressurized fluid (compressed air). Accordingly, suitable O-rings (here formed of BUNA-N rubber) are provided seated in channels indicated. Annular channel 210 is formed in the spool 74 near face 78 and O-ring 212 is seated therein.

Annular channel 214 seating O-ring 216 is formed in the flange 50 of end cap 36 for engagement with the facing end of sleeve 34. Annular channel 218 seating O-ring 220 is formed in the passage defining wall of end cap 36. Annular channel 222 is formed in the spool 74 near end face 76 and seats O-ring 224.

Flat end, stainless steel pins 226 are seated in diametrically opposed portions of the face 227 of end cap 36 and faces like pins in end face 76 of spool 74. Likewise, similar pins 228 are seated in end face 78 and matching pins 230 are seated in the end face of cylindrical portion 134 of cover 38. These pins all extend a fraction of an inch from their surrounding surfaces and provide the only contact between facing surfaces, as well as serving axially to locate the cross passageways in the spool with the corresponding bores in the sleeve and limit the extent of the stroke of the spool 74.

It should be understood that the invention can be embodied in a packless spool valve having merely a pair of flow paths through the sleeve and a single segmenting bore formed in the spool. The spool can move slidably relative to the paths to segment a known slug from one and transfer same to the other. The clearances between spool and sleeve are of the order of magnitude of 10 to 90 millionths of an inch and thereby no packing is necessary. This is in contrast to other known segmenting valves which are face valves, that is, one where the ports and measuring bores must have a planar relationship at their juncture. There does not appear to be any erosion of the facing mouths of said ports and measuring bores during operation of the valve.

What is sought to be protected under the patent laws of the United States is:

1. A liquid transfer valve assembly for use in a diluting system and comprising:
    a valve body having a through axial passageway;
    a valve element seated within said through axial passageway for reciprocable slidable movement linearly therein between load and delivery conditions;
    drive means communicatively coupled to said valve element for effecting movement of said valve element between the load and delivery conditions;
    cooperating limit means maintaining the linearity of the path followed by said valve element;
    means defining the extent of said path;
    said valve body having at least two sets of through passageway pairs defining flow paths through the valve body and said valve element having at least two sets of through bore pairs, at least one of each set of through bore pairs having a precise measuring volume and arranged to intercept said flow paths selectively to entrain a portion of liquid flowing in one flow path of each set at the load condition of the valve element and to segment and transfer the entrained portion to the other flow path of each set for delivery to a predetermined location at the delivery condition of said valve element, each set of through bore pairs being of different volume; and
    means for delivering the same volume of diluent to the said other flow path for effecting said delivery whereby at least two different volumes of liquid are segmented and delivered.

2. The liquid transfer valve assembly as claimed in claim 1 in which the members of each set of passageway and bore pairs are spaced axially the same linear distance one from the other, the valve element being translatable only to the extent of said linear distance.

3. The liquid transfer valve assembly as claimed in claim 2 in which said valve body is an open-ended sleeve carrying a uniform axial passage defining said chamber, means closing off said chamber comprising an end cap sealingly secured to said sleeve at one end thereof and a cover sealingly secured to said sleeve at the other end thereof; and said drive means includes passage means formed in the end cap and the cover leading to said chamber, means coupling a source of pressurized fluid to said passage means and means alternately feeding pressurized fluid to one end of the chamber while venting the opposite end of the chamber by way of said coupling means to drive the valve element reciprocably along its linear path.

4. The liquid transfer valve as claimed in claim 1 in which said valve element is formed of at least two portions, one portion being substantially less in cross section than the other and the said through axial passageway includes portions conforming in configuration to the valve element portions; one of said set of through passageway pairs defining one pair of flow paths through said one of said through axial passageway portions and said valve element having one set of through bore pairs formed in the lesser cross-section portion thereof.

5. The liquid transfer valve assembly as claimed in claim 4 in which said one set of through bore pairs are of lesser diameter than other sets of through bore pairs.

6. The liquid transfer valve assembly as claimed in claim 1 in which there is a third set of through passageway pairs formed through the valve body and a third set of through bore pairs formed in the valve element, means coupling said first and second sets to a source of a first sample to be segmented and means independently coupling said third set to another sample source.

7. The liquid transfer valve assembly as claimed in claim 6 in which one of said first and second sets of through bore pairs are of lesser segmenting volume than the other, and the third set of through bore pairs has a different segmenting volume.

8. The liquid transfer valve assembly as claimed in claim 7 in which said third set of through bore pairs has a segmenting volume greater than the segmenting volume of the first or second sets of through bore pairs.

9. The liquid transfer valve assembly as claimed in claim 1 and lubricating means for lubricating the bearing surfaces of said valve element simultaneously with at least one lineal translation thereof.

10. The liquid transfer valve assembly as claimed in claim 3 and lubricating means comprising lubricant reservoir means formed within said valve body, means for establishing communication between said valve element surface and said lubricant reservoir means, piston means within said reservoir means and means for introducing pressurized fluid to said piston means simultaneously with feeding thereof to the through axial passageway whereby lubricant is fed to said surface during at least one translation of the valve element.

11. The liquid transfer valve assembly as claimed in claim 1 in which the clearance for the said valve element is of the order of magnitude of 10 to 90 millionths of an inch.

12. The liquid transfer valve assembly as claimed in claim 11 and lubricating means for lubricating the bearing surfaces of said valve element simultaneously with at least one lineal translation thereof.

13. The liquid transfer valve assembly as claimed in claim 12 in which said means for driving the valve element comprises a source of pressurized fluid and means for introducing pulsed applications thereof to the ends of said valve element.

14. The liquid transfer valve assembly as claimed in claim 11 in which said valve body comprises an elongate sleeve having said axial passageway formed therein to define substantial portion of a chamber, an end cap sealingly secured to one end of the sleeve and a cover closing off the opposite end of the sleeve, the end cap having a passageway therein coaxial with and opening to the axial passageway of said sleeve, said passageway having a diameter less than said axial passageway and defining the remainder of a chamber; said valve element comprising a cylindrical spool having one portion of diameter selected to establish said clearance within said end cap passageway, one of said sets of flow path pairs being established through said less diameter portion of said chamber and one of said sets of through bore pairs being formed in the second portion of said spool, the spacing between axial centers of each set of through bore pairs being the same and said cooperating limiting means comprise a linear groove formed in said spool having a length at least equal to the length of permitted translation of said spool and a pin mounted in said sleeve and accommodated within said groove.

15. The liquid transfer valve assembly as claimed in claim 14 in which there is a third set of flow path pairs established through the greater diameter portion of said chamber and a third set of through bore pairs formed in the spool of selective interception of said third set of flow path pairs.

16. The liquid transfer valve assembly as claimed in claim 1 and a diluting system wherein the segmented volume of one set of through bore pairs is delivered to one testing apparatus and the segmented volume of the other set of through bore pairs is delivered simultaneously to a second testing apparatus, mixing of segmented liquid and diluent being performed within the respective testing apparatus to form the respective dilutions simultaneously.

17. The liquid transfer valve assembly as claimed in claim 15 and a diluting system wherein there is conduit means communicating from a first sample source to the first and second sets of flow paths and through bore pairs, second conduit means communicating from a second sample source to said third set of flow path and through bore pairs and means for feeding sample either from said first or from the second sample sources to their associated flow paths.

18. The liquid transfer valve assembly as claimed in claim 16 in which all mixing of segmented samples and diluent is performed in a single vessel of each associated testing apparatus.

19. The liquid transfer valve assembly as claimed in claim 1 and said drive means include means introducing compressed air in pulses alternatively to the ends of said valve element driving said valve element in its linear stroke.

20. The liquid transfer valve assembly as claimed in claim 17 in which compressed fluid is introduced to opposite ends alternately to the ends of the valve element in pulses of predetermined duration for segmenting and transferring fluid from said one of said third fluid path pairs to the other of said third fluid path pairs thereafter returning the valve to its initiate condition with only said one of said third measuring bore pairs communicating with said one of said third fluid path pairs whereby flow of sample is continuous through the valve along said one of said third fluid path pairs except for the duration of said segmentation.

21. A liquid transfer valve assembly for use in a diluting system wherein different volumes of a sample to be diluted are delivered to specified locations for mixing and operation performed thereon within testing apparatus and means for introducing reagent to the specified location of one of said testing apparatus for mixing with the diluted sample therein;

said transfer valve assembly comprising a spool valve arrangement having a sleeve defining a cylindrical chamber and a reciprocable cylindrical spool slidably linearly translatable within said chamber between first and second dispositive conditions;

means for sealingly closing off the opposite ends of said chamber, plural pairs of through passageways formed in the sleeve defining plural flow path pairs through said chamber, a like number of plural segmenting through bore pairs formed diametrically in said spool, each pair of segmenting bores having a different volume, one of said segmenting bore pairs communicating with one flow path of each flow path pair at a first dispositive condition of the spool and entraining a predetermined volume of liquid flowing through said one flow path, said one segmenting bore segmenting and transferring said volume to the other of said flow path pair at the second dispositive condition of said spool; and means for applying pressurized fluid to opposite ends of said spool to translate the spool from one dispositive condition to the other.

22. The liquid transfer valve assembly as claimed in claim 21 in which the chamber includes a narrow diameter portion and the spool has a narrow diameter portion sealingly slidably reciprocable within the narrow diameter chamber portion, at least one pair of said plural flow path pairs being established through said narrow diameter portions and at least a pair of segmenting bores formed in said narrow diameter portion of said spool and alignable with said one pair of flow path pairs.

23. A liquid transfer valve assembly as claimed in claim 21 in which the clearance between sleeve and spool is of the order of magnitude of 30 to 90 millionths of an inch.

24. A liquid transfer valve assembly as claimed in claim 23 and lubricating means operated by said pressurized fluid for lubricating said spool during its translatory movement.

25. A liquid transfer valve assembly as claimed in claim 23 in which said lubricating means comprise a plurality of lubricant reservoirs formed within said sleeve, a like number of linearly extending channels along the inner wall of said chamber and in communication with said reservoirs, piston means within said reservoirs and means for applying pulsed pressurized fluid applications to said piston means for introducing lubricant to said channels, the spool being in surface contact with the lubricant fed to said channels along a substantial proportion of the linear length thereof.

26. The liquid transfer valve assembly as claimed in claim 25 in which said channels are of crescentlike cross section.

27. The liquid transfer valve assembly as claimed in claim 20 in which the entrances and outlets of at least one of said pairs of passageways are conical to facilitate flow.

28. The liquid transfer valve assembly as claimed in claim 21 in which there are means for limiting the length of the stroke of said spool so that the respective passageways and segmenting bores are aligned during the first and second dispositive conditions of said spool.

29. A liquid transfer valve assembly for use in a diluting system comprising, an elongate body having a through axial passageway and means closing off the opposite ends of said passageway to define a chamber;

a movable valve element having a configuration conforming to said chamber, said valve element being seated within said chamber for frictional linear slidable movement therein;

drive means operable upon said valve element to reciprocate same within said chamber between two dispositive conditions;

said elongate body having at least two spaced sets of parallel through passageway pairs axially aligned one relative to the others, said passageway pairs opening to said chamber at diametrically opposed locations respectively to define pairs of liquid flow paths through said body;

said valve element carrying at least two spaced pairs of precise measuring bores, each member of a set of spaced bores being aligned with each member of a matching set of said passageways at one condition of said valve element and aligned with only one member of each set of said passageways at the other condition of said valve element; and said bores of a set carried by said valve element being identical in volume and the sets differing in volume so that liquid entrained in a bore of one set at one of said first and second conditions is segmented respectively and transferred for discharge at the other of said first and second conditions, different volumes of segmented liquid being discharged so that liquid introduced into one member of each set of bores is discharged with a given volume of diluent to deliver two different volumes simultaneously to separate locations for mixing to form two dilutions of differing degree.

30. The liquid transfer valve assembly as claimed in claim 29 in which said valve element and said chamber are cylindrical in configuration, the valve element is arranged in surface engagement with the inner cylindrical wall of said body which defines the chamber and lubricating means establishing a slidable sealed engagement between the body and the movable valve element.

31. The liquid transfer valve assembly as claimed in claim 30 in which said chamber comprises a pair of coaxial subchambers communicating directly one with the other, said subchambers being of different diameters and said valve element being of conforming configuration relative to said subchambers, one set of measuring bores being formed in the lesser diameter portion of said valve element and the other set formed in the other portion of said valve element.

32. The liquid transfer valve assembly as claimed in claim 29 and cooperating means on both valve element and body for maintaining said valve element in a solely linear path of movement.

33. The liquid transfer valve assembly as claimed in claim 29 in which the distance moved by said valve element between said first and second conditions is equal to the distance between axial centers of the members of said measuring bore sets.

34. The liquid transfer valve assembly as claimed in claim 1 in which said actuator means comprise a source of fluid pressure, conduit means leading said fluid pressure to opposite ends of said valve element and means to apply said fluid pressure periodically to said valve element.

35. The liquid transfer valve assembly as claimed in claim 34 in which said fluid pressure is led to the opposite ends of the larger diameter portion of said valve element.

36. The liquid transfer valve assembly as claimed in claim 30 in which the lubricating means comprises a pressurized silicone lubricant applied between said valve element and the chamber wall, a lubricant reservoir and piston means operable upon lubricant in the reservoir to pressurize said lubricant and driving same between said body and chamber wall during a translation of said valve element.

37. A liquid transfer valve for use in an automatic diluting system wherein a plurality of dilutions are produced from a single fluid sample and a source of diluent, said valve comprising
   an elongate central body;
   a pair of hollow outer bodies having a respective pair of axially aligned directly communicating different diameter chambers; said central body having a configuration conforming to said axially aligned chambers and being disposed therein for linear, slidable frictional reciprocable movement between first and second positions;
   cooperating guide means for limiting the movement of said central body to only a linear direction;
   means operable upon opposite ends of the central body for driving said central body;
   said central body having at least two sets of precise parallel measuring bore pairs formed therein passing through the axis thereof; and
   said outer body carrying at least two spaced sets of through passageways formed therein communicating with one member of each set of the measuring bores in one position of said central body and with both members of each set of measuring bores in the other position of said central body, each set of bores being different in volume, whereby at least two different segmented volumes of the sample are delivered to different locations along with a given respective volume of diluent from the source.

38. The liquid transfer valve as claimed in claim 37 in which there are means limiting the extent of linear movement of said central body.

39. The liquid transfer valve as claimed in claim 38 in which said last-mentioned means comprise a pin and groove coupling between central body and hollow body.

40. A transfer valve for use in a diluting system for providing at least a pair of different segmented samples the volume of one segmented sample being different than the volume of the other segmented sample of said pair, and the same volumes of diluent to form at least two dilutions of differing concentration simultaneously from a single fluid sample, and in which the transfer valve has a first portion for receiving and isolating therein an amount of the liquid sample and for combining said amount of sample with a first volume of a diluent to produce a precise desired first dilution; a first vessel for receiving said volumes and mixing same to form said first dilution; a second transfer valve portion for receiving and isolating therein a different amount of said sample and for combining said amount with the same quantity of diluent to produce a precise desired second dilution; a second vessel for receiving said second volumes and mixing same to form said second dilution and means for introducing said liquid sample into said first and second valve portions simultaneously and delivering same also simultaneously while directing diluent through said measuring portions for rinsing same, said transfer valve including at least a pair of elements in face to face contact, one of which is movable linearly relative to the other between first and second positions and has said first valve portion having a body of a given diameter and a pair of cross through bores formed therein and the second valve portion having a body of greater diameter and at least a second pair of cross through bores formed therein, all said bores being parallel and said second pair of cross through bores having a volume different from the volume of the first cross through bores, the members of each bore pair being spaced center to center the same distance, ports defining pairs of liquid passageways in the remainder of the valve structure of a diameter conforming to the pairs of parallel bores and capable of communicating therewith, when said movable valve element is in said first position, one of said bores is in communication with the other of each pair of liquid passageways, indexing of the movable valve element to the second position aligns one of each bore pair with one member each of said fluid passageway pairs while said one bore of each pair subtends an amount of liquid sample and deposits said amount for combining with the diluent to deliver said two segmented volumes and the same given volume of diluent simultaneously to two locations for forming two dilutions of different known degree of the same sample, said bores and ports being formed in the respective valve elements oriented parallel and in planes normal to the direction of movement of the movable valve element.

41. The fluid transfer valve as claimed in claim 40 in which there are means for pneumatically driving said movable element with alternate impulses of pressurized fluid from a source thereof applied to opposite ends of said movable element.

42. The liquid transfer valve as claimed in claim 41 in which said valve includes lubrication means for feeding lubricant to the bearing surfaces of the valve simultaneously with driving said movable element at least in one direction.

43. The liquid transfer valve as claimed in claim 42 in which said lubrication means includes a lubricant reservoir communicating with the interior of the valve, piston means within said reservoir and means for directing pressurized fluid against said piston means to force lubricant from the reservoir to the clearance of said sleeve and spool.

44. A liquid transfer valve for use in a diluting system and comprising a linearly movable valve element sandwiched between a pair of opposed facing conforming surfaces for frictionally slidable movement therebetween, said valve element having at least two spaced pair of parallel through bores and said stationary surfaces having ports opening thereto and to the exterior of the valve, the valve element being movable between a first position where said bores are each aligned with one of each set of ports and a second position where each of said bores are aligned with each of the ports of said pairs associated therrewith, the bores of a pair being of like volume but each pair being of different volume, means for driving the movable element along a limited solely linear path between first and second positions, the length of the path being limited to the distance between axial centers of the bores of each pair, and said means for driving comprises a source of pressurized fluid and conduit means for introducing said fluid alternately to opposite ends of said movable element.

45. The transfer valve as claimed in claim 44 in which the stationary surfaces comprised diametrically opposed facing surfaces defining an axial passageway formed in a body and the valve element comprises a plunger slidingly sealingly movable within said axial passageway, said plunger and said chamber having first and second integral portions of differing cross-sectional diameter, each portion carrying one set of bores and ports.

46. The liquid transfer valve as claimed in claim 45 in which said greater cross-section portions have an additional set of bores and ports formed therethrough spaced along the length thereof and being of different cross section, the members of said additional set being of like cross section.

47. The liquid transfer valve as claimed in claim 46 and separate means for directing liquid to and receiving liquid from one or the other of the sets which are formed in the greater cross-section portion.

48. In a diluting system, a liquid transfer valve assembly comprising,
   a sleeve having an axial through passage defining a chamber;
   a spool reciprocable only along a linear path within said chamber;
   at least two sets of flow path pairs established through the chamber;
   at least two sets of precise bore pairs formed diametrically through said spool, said sets being spaced along a common line along the length of said spool;
   each of said sets of bore pairs having a different volume, the members of the same set being identical; and
   means for translating said spool from a first position where one member of each set of bore pairs intercepts one member of each set of flow paths and a second position where both members of each set of bore pairs intercept both members of each set of flow paths to permit a volume of liquid to be entrained from one flow path of each set of flow path pairs at the first position of the spool and to be segmented and transferred to the other flow path of each set of flow path pairs at the second position of said spool.

49. The diluting system as claimed in claim 48 in which the clearance between sleeve and spool is of the order of 30 to 90 millionths of an inch.

50. The diluting system as claimed in claim 48 in which there are means coupling one of each flow path pairs to a source of diluent and dispenser means for delivering a predetermined identical volume of diluent to said one flow path during the disposition of said spool at its second position, delivering the different segmented volumes and accompanying diluent to two different locations simultaneously.

51. The diluting system as claimed in claim 48 in which there are conduit means coupling the other of each of said flow path pairs to a different testing apparatus, the segmented volume being directed to a vessel thereof along with the volume of diluent, and means for mixing the delivered volumes within said vessel to form the dilution.

52. The diluting system as claimed in claim 48 in which there are means for introducing a predetermined volume of reagent to the vessel of one testing apparatus for mixing with the contents thereof.

53. The diluting system as claimed in claim 48 in which there is an additional set of flow path pairs and bore pairs formed in the sleeve and spool respectively, and means for selectively introducing liquid sample from a source independently to said third set for segmentation of a precise volume thereof and transfer of said segmented volume to a second testing apparatus with the remaining volume from said source delivered to said vessel of said one testing apparatus.

54. The diluting system as claimed in claim 48 in which there are two independent testing apparatuses each having a vessel arranged each to receive one of the segmented samples and accompanying diluent respectively, and means for mixing the received volumes within said vessel.

55. The diluting system as claimed in claim 54 and means for introducing reagent into one of said vessels.

56. The diluting system as claimed in claim 48 in which one of the segmenting bore pairs is of different diameter than the other segmenting bore pair.

57. The diluting system as claimed in claim 48 in which there are three pairs of like segmenting bores, each pair having different volumes whereby to segment and transfer different volumes of liquid from one associated flow path to the other, said flow paths leading to at least two independent testing apparatus.

58. The diluting system as claimed in claim 48 in which the segmenting bores are formed diametrically through the spool in spaced pairs in a linear row, each pair being spaced along the length of the spool, the length of the path traversed by the spool being equal to the axial spacing center to center of the members of each pair.

59. The diluting system as claimed in claim 48 in which the spool has a lesser diameter portion carrying one of said pair of segmenting bores.

60. The diluting system as claimed in claim 48 and means for back rinsing one flow path of a pair while the segmented volumes are delivered to the other flow path of that pair.

61. A packless liquid transfer valve assembly for use in a diluting system and comprising:
   a valve body having a through passageway defining a chamber;
   a valve element seated within said chamber for slidable movement therein between load and delivery conditions;
   drive means communicatively coupled to said valve element for effecting movement of said valve element between the load and delivery conditions;
   means sealingly closing off said chamber;
   means defining the extent of movement of said valve element;
   said valve body having at least one set of through passageway pairs defining flow paths through the valve body and said valve element having at least one precise measuring bore pair arranged to intercept said flow paths selectively to entrain a portion of liquid flowing in one flow path of said set at the load condition of the valve element and to segment and transfer the entrained portion to the other flow path of said set for delivery to a predetermined location at the delivery condition of said valve element, the clearance between said valve body and said valve element being of the order of magnitude of 10 to 90 millionths of an inch and lubricating means effective on the bearing surfaces of said valve body and valve element for lubricating same with each movement of said valve element to said load and said delivery conditions so that a leakproof coupling between passageway pairs and said measuring bore is established in the absence of packing.

62. The packless liquid transfer valve assembly as claimed in claim 61 in which said valve body is an open-ended sleeve carrying a uniform axial passage defining said chamber and said valve element is a spool seated within said sleeve.

63. The packless liquid transfer valve assembly as claimed in claim 61 in which said valve element is reciprocable linearly within said chamber and said valve body and valve element having cooperating limit means maintaining the linearity of the path followed by said valve element.

64. The packless liquid transfer valve assembly as claimed in claim 62 in which said means closing off said chamber comprise an end cap sealingly secured to said sleeve at one end thereof and a cover sealingly secured to said sleeve at the other end thereof; and said drive means includes passage means formed in the end cap and the cover leading to said chamber, means coupling a source of pressurized fluid to said passage means and means alternately feeding pressurized fluid to one end of the chamber while venting the opposite end of the chamber by way of said coupling means to drive the valve element reciprocably along its linear path.

65. The packless liquid transfer valve assembly as claimed in claim 61 wherein said valve body has two sets of through passageway pairs defining flow paths through the valve body and said valve element has two sets of precise measuring bore pairs, the members of each set of measuring bore pairs being identical in volume but each set of measuring bore pairs being of different volume; and
 means for delivering the same volume of diluent to the said other flow path for effecting said delivery whereby at least two different volumes of liquid are segmented and delivered.

66. The packless liquid transfer valve assembly as claimed in claim 63 in which said means for driving the valve element comprises a source of pressurized fluid and means for introducing pulsed applications thereof to the ends of said valve element.

67. The packless liquid transfer valve assembly as claimed in claim 63 and said lubricating means for lubricating the bearing surfaces of said valve element operates to lubricate said surfaces simultaneously with at least one lineal translation thereof.

68. The packless liquid transfer valve assembly as claimed in claim 65 in which said valve body comprises an elongate sleeve having an axial passageway defining a substantial portion of said chamber, an end cap sealingly secured to one end of the sleeve and a cover closing off the opposite end of the sleeve, the end cap having a passageway therein coaxial with and opening to the axial passageway of said sleeve, said passageway having a diameter less than said axial passageway and defining the remainder of said chamber; said valve element comprising a cylindrical spool having one portion of diameter selected to establish said clearance within said end cap passageway, one of said sets of flow path pairs being established through said lesser diameter portion of said chamber and one of said sets of measuring bore pairs being formed in the second portion of said spool, the spacing between axial centers of each set of measuring bore pairs being the same and cooperating limiting means comprise a linear groove formed in said spool having a length at least equal to the length of permitted translation of said spool and a pin mounted in said sleeve and accommodated within said groove whereby to limit movement of the spool to a linear path.

69. The packless liquid transfer valve assembly as claimed in claim 68 in which there is a third set of flow path pairs established through the greater diameter portion of said chamber and a third set of measuring bore pairs formed in the spool for selective interception of said third set of flow path pairs.

70. The packless liquid transfer valve assembly as claimed in claim 65 in which one of said first and second sets of measuring bore pairs are of lesser segmenting volume than the other, and the third set of measuring bore pairs has a different segmenting volume.

71. The packless liquid transfer valve assembly as claimed in claim 65 in which one of said first and second sets of measuring bore pairs are of lesser segmenting volume than the other, and the third set of measuring bore pairs has a different segmenting volume and said third set of measuring bore pairs has a segmenting volume greater than the segmenting volume of the first or second sets of measuring bore pairs.

72. The packless liquid transfer valve as claimed in claim 65 in which said valve element is formed of at least two portions, one portion being substantially less in cross section than the other and the chamber includes portions conforming in configuration to the valve element portions; one of said set of passageway pairs defining one pair of flow paths through said one of said chamber portions and said valve element having one set of measuring bore pairs formed in the lesser cross-section portion thereof.

73. The packless liquid transfer valve assembly as claimed in claim 72 in which said one set of measuring bore pairs are of lesser diameter than other sets of measuring bore pairs.

74. The packless liquid transfer valve assembly as claimed in claim 72 in which there is a third set of passageway pairs formed through the valve body and a third set of measuring bore pairs formed in the valve element, means coupling said first and second sets to a source of a first sample to be segmented and means independently coupling said third set to another sample source.

75. The packless liquid transfer valve assembly as claimed in claim 65 and a diluting system wherein the segmented volume of one set of measuring bore pairs is delivered to one testing apparatus and the segmented volume of the other set of measuring bore pairs is delivered simultaneously to a second testing apparatus, mixing of segmented liquid and diluent being performed within the respective testing apparatus to form the respective dilutions simultaneously.

76. The packless liquid transfer valve assembly as claimed in claim 75 in which all mixing of segmented samples and diluent is performed in a single vessel of each associated testing apparatus.

77. In a diluting system, a liquid transfer valve assembly comprising,
 a sleeve having an axial through passage;
 a spool slidably movable within said axial passage;
 at least two flow paths established through the axial passage;
 at least one precise bore formed diametrically through said spool; and
 means for translating said spool from a first position where said precise bore intercepts one of said flow paths and a second position where the bore intercepts the other of said flow paths to permit a volume of liquid to be entrained from one flow path at the first position of the spool and to be segmented and transferred to the other flow path at the second position of said spool and the clearance between sleeve and spool is of the order of 10 to 90 millionths of an inch.

78. The diluting system as claimed in claim 77 in which said spool is linearly reciprocable within said axial passage.

79. The diluting system as claimed in claim 78 in which there are at least two spaced precise bores formed in said spool spaced along the length of said spool, one of said precise bores intercepting one of said flow paths at the first position and said one bore intercepting the other of said flow paths at the second position to segment and transfer a volume of liquid from said one flow path to the other flow path, said other precise bore intercepting said one flow path at said second position whereby flow through the first flow path is substantially continuous.

80. The diluting system as claimed in claim 77 in which said spool is linearly reciprocable within the axial passage; there are at least two sets of flow path pairs established through the said axial passage chamber; there are at least two sets of precise bore pairs formed diametrically through said spool, at least one bore of each set having a precise volume; each of said sets having a different volume; and the spool is translated from the first position where said one bore of each set of bore pairs intercepts one of each set of flow paths and the second position where both members of each set of bore pairs intercept both of each set of flow paths to permit a volume of liquid to be entrained from one flow path of each pair in the precise volume bore thereof at the first position of the spool and to be segmented and transferred to the other flow path of each pair at the second position of said spool.

81. The diluting system as claimed in claim 80 in which there are three pairs of like segmenting bores and three sets of flow paths respectively associated therewith, each pair having different volumes whereby to segment and transfer different volumes of liquid from one associated flow path to the other.

82. The diluting system as claimed in claim 77 in which there is a second bore formed in said spool parallel to said precise bore and said precise bore and second bore are arranged in a set spaced along the length of the spool, said precise bore intercepting one of said flow paths at the first position and intercepting the other of said flow paths at the second position to segment and transfer a volume of liquid from said one flow path to the other flow path, the second bore intercepting said one flow path at said second position whereby flow is continuous through the valve along said one flow path, the one flow path leading to one testing apparatus and the other flow path leading to a different testing apparatus.

83. A method of transferring liquid samples to two different locations substantially simultaneously using a single valve assembly comprising the steps of establishing two distinct flow paths through the valve from one source to two different locations, segmenting a precise quantity of liquid from one flow path to the other flow path while maintaining significantly uninterrupted flow along said first flow path.

84. The method as claimed in claim 83 and the step of utilizing a pair of segmenting passageways, placing only one of the segmenting passageways in communication with said one flow path and then placing said one segmenting passageway in communication with said other flow path and simultaneously placing the other of said pair of segmenting passageways in communication with said one flow path.

85. The liquid transfer valve assembly as claimed in claimed 17 in which compressed fluid is introduced to opposite ends alternately to the ends of the valve element in pulses of predetermined duration for segmenting and transferring fluid from said one of said third fluid path pairs to the other of said third fluid path pairs thereafter returning the valve to its initiate condition with only said one of said third measuring bore pairs communicating with said one of said third fluid path pairs whereby flow of sample is continuous through the valve along said one of said third fluid path pairs.

* * * * *